United States Patent [19]

Hofmann

[11] Patent Number: 4,481,147

[45] Date of Patent: Nov. 6, 1984

[54] PROCESS FOR PREPARING ALKYLESTERS OF SATURATED ALIPHATIC CARBOXYLIC ACIDS

[75] Inventor: Peter Hofmann, Marl, Fed. Rep. of Germany

[73] Assignee: Chemische Werke Hüls AG, Marl, Fed. Rep. of Germany

[21] Appl. No.: 512,322

[22] Filed: Jul. 11, 1983

Related U.S. Application Data

[63] Continuation-in-part of Ser. No. 125,482, Feb. 28, 1980, abandoned.

[30] Foreign Application Priority Data

Mar. 29, 1979 [DE] Fed. Rep. of Germany ....... 2912489

[51] Int. Cl.$^3$ ............................ C11C 3/02; C09F 5/08
[52] U.S. Cl. .............................. 260/410.9 R; 260/410; 260/410.6; 560/233
[58] Field of Search ...................... 260/410.6, 410.9 C, 260/410; 560/233

[56] References Cited

U.S. PATENT DOCUMENTS 3,883,587  5/1975  Isa ..................................... 260/410.6
3,935,228  1/1976  Keblys ............................. 260/410.6

*Primary Examiner*—John F. Niebling
*Attorney, Agent, or Firm*—Wells & Wells

[57] ABSTRACT

Alkylesters of saturated aliphatic carboxylic acids are prepared by reacting aliphatic monoolefins containing internal double bonds and having 6 to 20 carbon atoms with carbon monoxide and an alkanol having one hydroxyl function in the presence of a catalyst of a cobalt compound and a promoter where the promoter is pyridine, a non-ortho-substituted alkylpyridine or a mixture thereof.

The monoolefins can possibly contain paraffins and the reaction is carried out with:

(a) a promoter to cobalt ratio of 3/1 to 25/1;
(b) a cobalt concentration from 0.02 to 0.2 gram-atom of cobalt per mole of monoolefin;
(c) a temperature between 165° and 195° C.;
(d) a pressure from 150 to 300 bars;
(e) a molar ratio of alkanol to monoolefin from 1/1 to 10/1; and
(f) a dwell time exceeding 15 minutes.

20 Claims, No Drawings

PROCESS FOR PREPARING ALKYLESTERS OF SATURATED ALIPHATIC CARBOXYLIC ACIDS

This application is a continuation-in-part of application Ser. No. 125,482, filed 2/28/80 abandoned.

BACKGROUND OF THE INVENTION

The field of the invention is synthetically produced higher fatty esters and the present invention is particularly concerned with fatty acid esters produced from internal olefins, carbon monoxide and lower alkanols in the presence of a catalyst containing cobalt.

It is known that by reacting olefins with carbon monoxide and an appropriate compound containing a replaceable hydrogen atom such as water, alkanol and amine in the presence of a catalyst containing a metal of Group VIII of the periodic table of elements and a promoter, fatty acids or the corresponding fatty acid derivatives are prepared as disclosed by J. Falbe in Synthesen mit Kohlenmonoxid (Synthesizing with carbon monoxide), Springer publisher, Berlin, Heidelberg, New York, (1967).

This reaction, known as alkoxycarbonylation, is most of all used to prepare fatty acid esters. In most cases α-olefins are reacted with lower alkanols having 1 to 8 carbon atoms in the presence of catalysts containing cobalt or nickel. The catalytic systems consisting of a cobalt compound and pyridine or a non-ortho-substituted pyridine derivative are found to be especially active. These systems at the same time are characterized by producing reaction products having high linearity. Furthermore, they extensively suppress the hydroformylation taking place as a side reaction and yield, as is known, aldehydes and acetals as disclosed in U.S. Pat. No. 3,507,891; British Pat. No. 1 269 525 and German Published application Nos. 16 18 156 and 19 63 804, the disclosures of which are incorporated herein.

While as a rule the state of the art as disclosed in these U.S., British and German patents do not exclude the use of olefins with internal double bonds, however, the specific examples of these prior art references show that unsatisfactory results are obtained for olefins with internal double bonds when they are reacted under conditions which are favorable to alpha-olefins. Thus, the rate of formation and the linearity of the esters produced from olefins with internal double bonds are strongly decreased, or only inadequate selectivity is achieved.

SUMMARY OF THE INVENTION

Having in mind the limitations of the prior art, it is an object of the present invention to carry out an alkoxycarbonylation process using monoolefins with internal double bonds, preferably mixtures of aliphatic monoolefins containing predominantly internal double bonds with results equal to or nearly equal to alpha-olefins for the criteria space-time yield, linearity and selectivity.

This object is achieved in the present invention by reacting aliphatic monoolefins having 6-20 carbon atoms and containing internal double bonds or a mixture of aliphatic monoolefins containing 50-100% by weight monoolefins having internal double bonds with carbon monoxide and alkanol in the presence of a catalyst consisting of a cobalt compound and a promoter from the group pyridine, non-orthosubstituted alkylpyridines or mixtures thereof at increased pressure and elevated temperatures, the monoolefins possibly containing paraffins, at:

(a) a promoter to cobalt ratio of about 3/1 to 25/1;
(b) a cobalt concentration from about 0.02 to 0.2 gram-atom of cobalt per mole of monoolefin;
(c) a temperature between about 165° and 195° C.;
(d) a pressure from about 150 to 300 bars;
(e) a molar ratio of alkanol to monoolefin from about 1/1 to 10/1; and
(f) a dwell time exceeding 15 minutes.

DESCRIPTION OF THE PREFERRED EMBODIMENTS

The aliphatic monoolefins having internal double bonds as used in the process of the present invention as a rule are prepared by methods known to the state of the art from paraffins by dehydrogenation or chlorination and subsequent dehydrochlorination of the chloroparaffins obtained. Such a prior art process is disclosed in British Pat. No. 1 037 868. In these methods, cuts of paraffin, that is mixtures of different carbon numbers, are used as a rule, whereby the olefins obtained in turn lack a uniform number of carbon atoms. Furthermore, any conceivable isomeric form can appear in these mixtures of olefins.

Besides the pure monoolefins having 6 to 20 carbon atoms and mixtures of them, the process of the present invention has in mind using such monoolefins with a paraffin content. The paraffin content arises from the fact that no complete conversion is achieved in the preparation of the olefins, and because the non-converted paraffins are not separated or only incompletely separated. Thus, an olefin-paraffin mixture obtained by chlorination-dehydrochlorination contains about 70% by weight of paraffin. Olefin-paraffin mixtures suitable for use in the present invention have a paraffin content in the % by weight of 50 to 95 and preferably 60 to 85.

In the embodiment where a mixture of monoolefins is also mixed with paraffins, the preferred ranges of components in % by weight are:

aliphatic monoolefins without internal double bonds 0 to 25, aliphatic monoolefins with internal double bonds 2.5 to 50, and paraffins 50 to 95.

The carbon monoxide used is obtainable from synthesis gas by known separation methods such as low temperature distillation and molecular sieve separation. It is not necessary to remove the hydrogen quantitatively, because a hydrogen content not exceeding about 10% by volume is known from experience to favorably affect the rate of reaction. On the other hand, all impurities which degrade the activity of the catalyst system must be extensively removed.

The alkanols used in the process of the present invention are all primary and secondary alkanols with one hydroxyl function. Preferred alkanols are those with carbon numbers up to and including 4, that is, methanol, ethanol, propanol, isopropanol, n-butanol, isobutanol and butanol-2. If the reprocessing of the reaction mixture does not call for a higher alkanol, methanol is preferred as the esterification component.

The catalyst used consists of a cobalt compound and a promoter. Suitable cobalt compounds are carbonyls such as dicobaltoctacarbonyl, i.e., carboxylic acid salts of cobalt, such as cobalt acetate, cobalt naphthenate, cobalt 2-ethylhexanoate and cobalt stearate. Furthermore, carbonates and oxides of cobalt are also useful.

The cobalt may be present in any valence in these compounds. Applicable promoters are pyridine and all non-orthosubstituted halogen free pyridine derivatives such as beta-picoline and gamma-picoline, 3,4-lutidine and 3,5-lutidine and gamma-ethylpyridine.

The ratio of promoter to cobalt used is in the range from about 3/1 to 25/1. In this ratio, the promoter is denoted in moles and the cobalt compound is in gram-atoms of cobalt. Within the range from about 3/1 to 25/1, the range from 5/1 to 15/1 is preferred when paraffin-free or extensively paraffin-free monoolefin (<5% by weight of paraffin) is used and the range from about 10/1 to 25/1 is preferred when monoolefins containing paraffin (up to about 80% by weight of paraffin) are used. The optimal range shifts correspondingly when monoolefins are used with paraffin contents between these extremes. This also applies for the optimal ranges below process-critical steps.

The useful cobalt concentration is from about 0.02 to 0.2 gram-atoms of cobalt per mole of monoolefin. The range from 0.02 to 0.08 is preferred when paraffin-free monoolefins are used and that from 0.08 to 0.2 when monoolefins are used with paraffin.

The process of the present invention is carried out at a temperature between about 165° and 195° C., preferably between 175° and 185° C.

The pressure used is within the range from about 150 to 300 bars, preferably between 180 and 270 bars.

The molar ratio of alkanol to monoolefin used is from about 1/1 to 10/1. The range from 1/1 to 4/1 is preferred when paraffin-free monoolefins are used and that from 4/1 to 10/1 is preferred when monoolefins containing paraffin are used.

The dwell time—which is defined as the quotient of the liquid-filled reactor volume divided by the sum of the volumes fed in per unit time of input substances liquid at 50° C.—exceeds 15 minutes in the process of the present invention and ranges from 15 to 300 minutes. For paraffin-free monoolefins preferably a dwell time equal to or larger than 30 minutes is selected, and for monoolefins containing paraffin, a dwell time equal to or larger than 60 minutes. There is no critical upper limit of the dwell time, rather it results from the production output per unit time desired for a given volume of reaction.

In general, the process of the present invention is carried out in such a manner that where appropriate monoolefins containing paraffin are pretreated together with the alkanol, the promoter and the cobalt compound in an autoclave-equipped mixer and the oxygen is removed by rinsing with an inert gas. After the desired temperature of reaction is set, carbon monoxide is impressed. By an automatically controlled internal cooling and by repeated application of carbon monoxide, both the temperature and pressure can be kept constant. If a carbonyl is used as the cobalt compound, it is recommended that it be applied during the phase of temperature-raising a carbon monoxide pressure in order to assure the stability of the carbonyl. The reaction can be monitored by gas-chromatographic analysis of samples removed in the course of the reaction. When the desired conversion has been reached, the reaction is terminated by cooling the contents of the autoclave and by subsequent decompression.

In a preferred embodiment of the present invention, the reaction mixture is treated at a temperature between about 20° and 100° C., preferably between 40° and 60° C. with an oxygenated gas, preferably air, until the cobalt compounds which result in the separation of metallic cobalt during the processing by distillation are destroyed by oxidation. This embodiment can be carried out for instance in a trickling column by circulating the oxygenated gas in counterflow to the reaction discharge. The destruction by oxidation is easily recognized in the change in color (from brown-orange to brown-violet).

Following the treatment with an oxygenated gas, the reaction discharge is reprocessed by distillation. It is possible to proceed either in such manner that first unconverted alkanol and monoolefin as well as promoter, where appropriate paraffin and reaction products, are separated from the cobalt-containing residue and then are subjected to fractionating distillation, or else to carry out the fractionated distillation without prior separation of the cobalt compounds. The alcohol, monoolefin, promoter and the cobalt-containing residue may be recycled into the process.

The process of the present invention can be carried out discontinuously as well as continuously. As regards the continuous procedure, it may be appropriate in many cases to undertake catalytic preformation. It is possible to proceed for instance in such a manner that the cobalt compound soluble in pyridine or in pyridine derivatives is treated in a separate reaction stage at higher temperatures (120° to 200° C.) and at a higher pressure (100 to 300 bars) with hydrogenated carbon monoxide (1 to 60% by volume of $H_2$). The cobalt compound used can also be in the form of the cobalt-containing residue obtained by the distillative reprocessing of the alkoxycarbonylation mixture. The preformed catalyst is used together with the monoolefin which may contain paraffin and with the alkanol in the alkoxycarbonylation stage.

The alkylester-saturated aliphatic carboxylic acids prepared by the process of the present invention are used as the raw materials for fatty alcohols, fatty acids and fatty amines and for their derivatives. Fatty alcohols can be obtained by hydrogenation with copper chromite catalysts, fatty acids by hydrolysis and fatty amines by reaction with ammonia and subsequent hydrogenation from the corresponding esters. These products and their derivatives are applied for instance as raw materials for detergents, components for lubricants, emulsifiers and plasticizers.

The present invention is discussed in further detail below with particular reference to the specific examples and comparison examples.

Unless otherwise specified, all percentage data are in % by weight or mole %.

EXAMPLE 1

168 Parts by weight of a statistical isomeric mixture of internal n-dodecenes having an alpha-olefin proportion of less than 1% are placed into a stainless steel autoclave with 64 parts by weight of methanol, 29.5 parts by weight of cobalt naphthenate containing 10% by weight of cobalt and 46.5 parts by weight of gamma-picoline. These input quantities represent a molar ratio of methanol to olefin=2/1; of cobalt to olefin=0.05/1; and of gamma-picoline to cobalt=10/1. Following heating to 180° C., first 2.5 bars of $H_2$ are applied by means of a metering vessel and by next applying carbon monoxide (CO), a total pressure of 180 bars is set, which by multiple reapplication of CO is kept constant within +/−3 bars. The reaction is monitored by removing samples which are analyzed by gas liquid chromatography over a period of 6 hours. For an olefin conversion of 60%, there is a space-time yield of 370 g of tridecanoic acid methyl ester per hour and per liter with the reactor volume filled with liquid. For a 60% olefin conversion, the selectivity with respect to tridecanoic acid methylesters is 95%, the proportion of the linear (n-) tridecanoic acid methylesters (referred to the sum of the isomerous tridecanic acid methyl esters) is 74%.

EXAMPLES 2 AND 3

The process described in Example 1 is repeated while maintaining the conditions of reaction and the molar ratios of the input materials, with 8.55 parts by weight of $Co_2(CO)_8$ or 12.45 parts by weight of $Co(CH_3COO)_2 \cdot 4H_2O$ as catalytic first stage in lieu of Co-naphthenate.

TABLE 1

| Example | Catalytic first stage | Space-time yield* g/l · h | Ester Selectivity* % | Linear ester Proportion* % |
|---|---|---|---|---|
| 2 | $Co_2(CO)_8$ | 400 | 95 | 73 |
| 3 | $Co(CH_3COO)_2 \cdot 4H_2O$ | 360 | 94 | 74 |

*for 60% olefin conversion

EXAMPLE 4

The process described in Example 1 is repeated keeping the conditions of reaction and molar ratios of the input materials, with 39.5 parts by weight of pyridine in lieu of gamma-picoline. For an olefin conversion of 60% there results a space-time yield of 320 g of tridecanoic acid methylester per hour and per liter for a liquid-filled reactor volume. The selectivity is 94% and the proportion of linear esters is 72%.

EXAMPLE 5

593 Parts by weight of a mixture of 425 parts by weight of n-dodecane and 168 parts by weight of a statistical isomeric mixture of internal n-dodecenes with a proportion of less than 1% of alpha-olefin are prepared in a stainless steel autoclave with 256 parts by weight of methanol, 82.5 parts by weight of cobalt naphthenate with a content of 10% by weight of cobalt and with 130 parts by weight of gamma-picoline. These input quantities represent molar ratios of methanol to olefin = 8/1; cobalt to olefin = 0.14/1; and gamma-picoline to cobalt = 10/1. After heating to 180° C., first 3.5 bars of $H_2$ are applied by means of a metering vessel and then a total pressure of 250 bars is set by applying CO, and said total pressure is kept constant within +/−5 bars by repeated application of CO. The reaction is monitored by removing samples which are analyzed in gas liquid chromatography over a period of 6 hours. For an olefin conversion of 60% there is a space-time yield of 100 g of tridecanoic acid methylester per hour and per liter of liquid-filled reactor space. For 60% olefin conversion, the selectivity with respect to tridecanoic acid methylester is 96%, the proportion of linear tridecanoic acid methylester (referred to the sum of isomeric tridecanoic acid methylesters) is 75%.

EXAMPLES 6 AND 7

The process described in Example 5 is repeated while maintaining the conditions of reaction and the molar ratios of the input materials, except that the mixture of paraffin and olefin in Example 5 is replaced by the following mixtures:

Example 6:
- 14 parts by weight of statistical n-decene isomer mixture (less than 1% of alpha);
- 138.6 parts by weight of statistical n-undecene isomer mixture (less than 1% of alpha);
- 36 parts by weight of decane; and
- 356.5 parts by weight of undecane.

Example 7:
- 134.4 parts by weight of statistical n-dodecene isomer mixture (less than 1% of alpha);
- 36.4 parts by weight of statistical tridecene isomer mixture (less than 1% of alpha);
- 345.5 parts by weight of dodecane; and
- 93.5 parts by weight of tridecane.

TABLE 2

| Example | C number of olefin-paraffin mixture | Space-time yield g/l · h* | Ester Selectivity mole %* | Linear Ester* Proportion mole % |
|---|---|---|---|---|
| 6 | $C_{10,11}$ | 110 | 96 | 76 |
| 7 | $C_{12,13}$ | 95 | 96 | 74 |

*for a conversion of 60 mole % of olefin.

EXAMPLES 8–12

The process described in Example 5 is repeated keeping the conditions of reaction and molar ratios of the input materials except that methanol is replaced by equimolar amounts of higher alkanols. The results obtained for an olefin conversion of 60% are listed in the table below.

TABLE 3

| Example | Alkanol | Space-Time yield, mole ester/l · h | % ester selectivity | Linear ester proportion, % |
|---|---|---|---|---|
| 8 | ethanol | 0.32 | 96 | 74 |
| 9 | propanol | 0.21 | 95 | 74 |
| 10 | propanol-(2) | 0.24 | 95 | 76 |
| 11 | butanol | 0.19 | 96 | 73 |
| 12 | 2-methyl-propanol | 0.16 | 95 | 72 |

EXAMPLE 13

Continuous alkoxycarbonylation reaction with separate catalyst preforming:

(a) catalyst preforming

A mixture of 29.5 parts by weight of cobalt naphthenate with a content of 10% by weight of cobalt and 46.5 parts by weight of gamma-picoline is reacted in an autoclave with synthesis gas (with equal proportions of $H_2$ and CO) at a temperature of 170° C. and a pressure of 160 bars in continuous manner with an average dwell time of 0.5 hours.

(b) alkoxycarbonylation

The catalyst system described in (a) and consisting of 29.5 parts by weight of cobalt naphthenate with a content of 10% by weight of cobalt and 46.5 parts by weight of gamma-picoline is reacted together with 168 parts by weight of a statistic isomeric mixture of internal n-dodecenes (alpha portion less than 1%) and 64 parts by weight of methanol with carbon monoxide at a temperature of 180° C. and a pressure of 200 bars with an average dwell time of 1.2 hours. (These input materials represent molar ratios of methanol to olefin = 2/1; cobalt to olefin = 0.05/1; and gamma-picoline to cobalt=10/1). In this manner an olefin conversion of 57% is obtained. The mixture of isomeric tridecanoic acid methylesters has a proportion of n- of 74% and a selectivity of 97%.

EXAMPLE 14

The process described in Example 13 is repeated while maintaining the conditions of reaction and the molar ratios of the input materials except that no catalytic preforming is carried out. (The temperature of reaction in the preforming stage is lowered to 20° C.). An olefin conversion of 51% is achieved. The mixture of isomeric tridecanoic acid methylesters so formed has an n-proportion of 73% and a selectivity of 98%.

EXAMPLE 15

Continuous alkoxycarbonylation with separate catalyst preforming:

(a) catalyst preforming:

A mixture of 100.3 parts by weight of cobalt naphthenate with a content of 10% by weight of cobalt and 158 parts by weight of gamma-picoline is reacted with synthesis gas according to the conditions described under 13 (a).

(b) alkoxycarbonylation:

The catalytic system consisting of 100.3 parts by weight of cobalt naphthenate with a content of 10% by weight of cobalt and 158 parts by weight of gamma-picoline and prepared as described in (a) is reacted together with 609.8 parts by weight of a mixture of 134.4 parts by weight of a statistical n-dodecene isomer mixture (alpha proportion less than 1%)

36.4 parts by weight of statistical n-tridecene isomer mixture (alpha proportion less than 1%);

345.5 parts by weight of dodecane; and 93.5 parts by weight of tridecane and 256 parts by weight of methanol with carbon monoxide at a temperature of 180° C. and a pressure of 250 bars. (The above quantities amount to molar ratios of methanol to olefin=8/1; cobalt to olefin=0.17/1; and gamma-picoline to cobalt=10/1). In this manner an olefin conversion of 62 mole % is obtained. The mixture of isomeric tridecaneoic acid methylesters and tetradecanoic acid methylesters has a selectivity of 95 mole % and an n-proportion of 75 mole %.

(c) reprocessing:

1,000 g/h of the reaction mixture obtained under (b) are treated at a temperature of 55° C. in a trickling column filled with Raschig rings (ID=2 cm; length=100 cm) in counterflow with 50 1/h of air.

The reaction mixture post-treated by oxidation is subjected to a fractionating distillation. Following separation of methanol gamma-picoline, unconverted olefin, paraffin and tridecanoic acid methylesters and tetradecanoic acid methylesters, 105 g of a cobalt-containing residue are obtained, which following dissolution for instance in gamma-picoline can be fed back as first catalytic stage into the reaction.

COMPARISON EXAMPLES A AND B

The process described in Example 1 is repeated, while maintaining the conditions of reaction and the molar ratios of the input materials, except that other ratios are selected from gamma-picoline to cobalt. Table 4 shows the results obtained for an olefin conversion of 60%.

COMPARISON EXAMPLE C

The process described in Comparison Example B is repeated, while maintaining the conditions of reaction and the molar ratios of the input materials, except that the gamma-picoline is replaced by an equimolar amount of pyridine. The results obtained for an olefin conversion of 60% are listed in Table 4.

TABLE 4

| Comparison Example | Promoter | Promoter/Cobalt Ratio | Space-Time Yield g/l · h | Ester Selectivity % | % Proportion of linear esters |
|---|---|---|---|---|---|
| A | gamma-picoline | 2.5 | 60 | 80 | 65 |
| B | gamma-picoline | 35 | 40 | 95 | 60 |
| C | pyridine | 35 | 80 | 95 | 66 |

COMPARISON EXAMPLES D AND E

The process described in Example 1 is repeated, while maintaining the conditions of reaction and the molar ratios of the input materials except for the reaction temperature. The table below lists the results obtained for an olefin conversion of 60%.

TABLE 5

| Comparison Example | Reaction Temp. °C. | Space-Time Yield g/l · h | Ester Selectivity % | % Proportion of linear esters |
|---|---|---|---|---|
| D | 150 | 40 | 97 | 52 |
| E | 200 | 10 | 81 | 70 |

COMPARISON EXAMPLES F AND G

The process described in Example 1 is repeated while maintaining the molar ratios of the input materials and the conditions of reaction except for the total pressure. The results obtained for an olefin conversion of 60% are listed below.

TABLE 6

| Comparison Example | Total Pressure, bars | Space-Time Yield g/l · h | % Ester Selectivity | % Linear ester Proportion |
|---|---|---|---|---|
| F | 60 | 50 | 93 | 78 |
| G | 350 | 300 | 95 | 55 |

COMPARISON EXAMPLE H

The process described in Example 1 is repeated while maintaining the same conditions of reaction and molar ratios as the input materials, except that another molar ratio of methanol to olefin is selected. The results obtained for an olefin conversion of 60% are listed in Table 7.

COMPARISON EXAMPLE J

The process described in Example 5 is repeated, while maintaining the same conditions of reaction and molar ratios of the input materials except for a total pressure of 200 bars (in lieu of 250 bars), with an equimolar amount of pyridine (in lieu of gamma-picoline) and with a molar ratio of methanol to olefin = 15/1 (in lieu of 8/1). The results obtained for an olefin conversion of 60% are listed in Table 7.

TABLE 7

| Comparison Example | Methanol to olefin ratio | Space-Time Yield g/l · h | % Ester Selectivity | % Linear Ester Proportion |
|---|---|---|---|---|
| H | 6/1 | 30 | 95 | 73 |
| J | 15/1 | 25 | 94 | 71 |

COMPARISON EXAMPLE K

The process described in Example 15 is repeated, while maintaining the conditions of reaction and the molar ratios of the input materials except that while retaining the ratio of 10/1 for gamma-picoline to cobalt, a ratio of 0.01/1 is selected for cobalt to olefin (in lieu of 0.17/1). In this matter an olefin conversion of 10 mole % is obtained. The mixture of isomeric tridecanoic acid methylesters and tetradecanoic acid methylesters has a selectivity of 92 mole % and a proportion of n- of 78 mole %.

COMPARISON EXAMPLE L

The process described in Example 13 is repeated while maintaining the same conditions of reaction and molar ratios of input substances except that while retaining the ratio of 10/1 for gamma-picoline to cobalt, a ratio of 0.015/1 (in lieu of 0.05/1) is selected for cobalt to olefin. An olefin conversion of 25% is obtained in this manner. The mixture of isomeric tridecanoic acid methylesters has a selectivity of 92 mole % and an n-portion of 77%.

COMPARISON EXAMPLE M

The process described in Example 13 is repeated while maintaining the same conditions of reaction and molar ratios of the input substances except that an average dwell time of 0.25 hours is selected for the alkoxycarbonylation stage. In this manner, a conversion of 25% is obtained. The mixture of isomeric tridecanoic acid methylesters has a selectivity of 93 mole % and an n- portion of 77%.

COMPARISON EXAMPLE N

The process described in Example 15 is repeated while maintaining the conditions of reaction and the molar ratios for the input substances except that an average dwell time of 0.5 hours is selected for the alkoxycarbonylation stage. In this manner one obtains a conversion of 10 mole %. The mixture of isomeric tridecanoic acid methylesters and tetradecanoic acid methylesters has a selectivity of 88 mole % and an n- portion of 80 mole %.

I claim:

1. A process for preparing more than about 72% linear alkylesters of saturated aliphatic carboxylic acids consisting essentially of reacting aliphatic monoolefins having 6 to 20 carbon atoms containing 50-100% by weight of said monoolefins having internal double bonds with carbon monoxide and a lower aliphatic alkanol having one hydroxyl function in the presence of a catalyst consisting of a cobalt compound selected from the group consisting of cobalt carbonyls, carboxylic acid salts of cobalt, cobalt carbonates and cobalt oxides and a promoter selected from the group consisting of pyridine and non-ortho lower alkyl substituted pyridine and mixtures thereof at a temperature of about 165° to 195° C., a pressure of about 150 to 300 bars, a dwell time in excess of 15 minutes, a promoter to cobalt ratio of about 3/1 to 25/1 where the promoter is measured in gram-atoms of cobalt, a cobalt concentration from about 0.02 to 0.2 gram-atoms of cobalt per mole of monoolefin, and a molar ratio of alkanol to monoolefin of about 1/1 to 10/1.

2. The process of claim 1 wherein said aliphatic mixture contains predominantly internal double bonds obtained by chlorinating paraffins with subsequent dehydrochlorination of the chloroparaffins so prepared.

3. The process of claim 1 wherein methanol is said alkanol.

4. The process of claim 1, wherein the reaction mixture is treated at temperatures between about 20° and 100° C. with an oxygenated gas, and uncoverted reactants, the promoter and the reaction products are seperated by distillation, and cobalt-containing residue is recycled.

5. The process of claim 1 wherein said alkanol is selected from the group consisting of methanol, ethanol, propanol, isopropanol, n-butanol, isobutanol, and butanol 2.

6. The process of claim 1, wherein said promoter to cobalt ratio is 5:1 to 15:1, said cobalt concentration is 0.02 to 0.08 and said molar ratio of alkanol to monoolefin is 1:1 to 4:1.

7. The process of claim 1, wherein said dwell time is 15 to 300 minutes.

8. The process of claim 7, wherein said temperature is 175° to 185° C. and said pressure is 180-270 bars.

9. The process of claim 1, wherein said alkylesters are 74% linear said temperature is 180° C., said pressure is 177 to 183 bars, said dwell time is 6 hours, said promoter to cobalt ratio is 10/1, said cobalt concentration is 0.05/1 and said molar ratio of alkanol to monoolefin is 2/1.

10. The process of claim 1, wherein said alkylesters are 74% linear said temperature is 180° C., said pressure is 200 bars, said dwell time is 1.2 hours said promoter to cobalt ratio is 10/1, said cobalt concentration is 0.05/1, and said molar ratio of alkanol to monoolefin is 2/1.

11. The process of claim 9, wherein said aliphatic monoolefins are an isomeric mixture of internal n-dodecenes, said alkanol is methanol, said cobalt compound is cobalt naphthenate and said promoter is gamma-picoline.

12. The process of claim 9, wherein said alkylesters are 73% linear said aliphatic monoolefins are an isomeric mixture of internal n-dodecenes, said alkanol is methanol, said cobalt compound is $Co_2(CO)_8$ and said promoter is gamma-picoline.

13. The process of claim 9, wherein said alkylesters are 74% linear said aliphatic monoolefins are an isomeric mixture of internal of internal n-dodecenes, said alkanol is methanol, said cobalt compound is $Co(CH_3COO)_2.H_2O$ and said promoter is gamma-picoline.

14. The process of claim 10, wherein said aliphatic monoolefins are an isomeric mixture of internal n-dodecenes, said alkanol is methanol, said cobalt compound is cobalt naphthenate and said promoter is gamma-picoline.

15. A process for preparing more than about 72% linear alkylesters of saturated aliphatic carboxylic acids consisting essentially of reacting aliphatic monoolefins having 6 to 20 carbon atoms containing 50–100% by weight of said monoolefins having internal double bonds and paraffins mixed with said monoolefins with carbon monoxide and a lower aliphatic alkanol having one hydroxyl function in the presence of a catalyst consisting of a cobalt compound selected from the group consisting of cobalt carbonyls, carboxylic acid salts of cobalt, cobalt carbonates and cobalt oxides and a promoter selected from the group consisting of pyridine and non-ortho lower alkyl substituted pyridine and mixtures thereof at a temperature of about 165° to 195° C., a pressure of about 150 to 300 bars, a dwell time in excess of 15 minutes, a promoter to cobalt ratio of about 3/1 to 25/1 where the promoter is measured in gram-atoms of cobalt, a cobalt concentration from about 0.02 to 0.2 gram-atoms of cobalt per mole of monoolefin, and a molar ratio of alkanol to monoolefin of about 1/1 to 10/1.

16. The process of claim 15, wherein said aliphatic monoolefins with internal double bonds are 2.5 to 50% by weight, and said paraffins are 50 to 95% by weight.

17. The process of claim 16, wherein said promoter to cobalt ratio is 10:1 to 25:1, said cobalt concentration is 0.08 to 0.2 and said molar ratio of alkanol to monoolefin is 4:1 to 10:1.

18. The process of claim 16, wherein said alkylesters are 75% linear said temperature is 180° C., said pressure is 245 to 255 bars, said dwell time is 6 hours, said promoter to cobalt ratio is 10/1, said cobalt concentration is 0.14/1, and said molar ratio of alkanol to monoolefin is 8/1.

19. The process of claim 18, wherein said paraffins are a mixture of 72% by weight n-dodecene and said aliphatic monoolefins are 28% by weight of an isomeric mixture of internal n-dodecenes, said alkanol is methanol, said cobalt compound is cobalt naphthenate and said promoter is gamma-picoline.

20. The process of claim 16, wherein said temperature is 180° C., said pressure is 250 bars, said promoter to cobalt ratio is 10/1, said cobalt concentration is 0.17/1, said molar ratio of alkanol to monoolefin is 8/1, said aliphatic monoolefins are 22% by weight of an isomeric mixture of internal n-dodecenes, 6% by weight of an isomeric mixture of internal n-tridecenes, said paraffins are 57% by weight of dodecane and 15% by weight of tridecane, said alkanol is methanol, said cobalt compound is cobalt naphthenate and said promoter is gamma-picoline.

* * * * *